United States Patent [19]

Kricsfalussy et al.

[11] Patent Number: 5,504,260
[45] Date of Patent: Apr. 2, 1996

[54] CATALYTIC OXIDATION

[75] Inventors: Zoltan Kricsfalussy; Helmut Waldmann; Hans-Joachim Traenckner, all of Leverkusen, Germany

[73] Assignee: Bayer Aktiengesellschaft, Leverkusen, Germany

[21] Appl. No.: 303,970

[22] Filed: Sep. 9, 1994

[30] Foreign Application Priority Data

Sep. 17, 1993 [DE] Germany .......................... 43 31 671.9

[51] Int. Cl.⁶ .......................... C07C 37/58; C07C 37/60
[52] U.S. Cl. .......................... 568/771; 568/741; 568/763; 568/800; 568/802
[58] Field of Search .......................... 568/741, 763, 568/771, 800, 802

[56] References Cited

U.S. PATENT DOCUMENTS

| 3,859,365 | 1/1975 | Young ..................... | 568/771 |
| 4,515,983 | 5/1985 | Goel et al. ............... | 560/130 |
| 4,982,015 | 1/1991 | Chao et al. .............. | 568/802 |
| 4,992,600 | 2/1991 | Chao et al. .............. | 568/802 |

FOREIGN PATENT DOCUMENTS

| 4-178341 | 6/1992 | Japan ..................... | 568/802 |
| 4244039 | 9/1992 | Japan . | |
| 6001738 | 1/1994 | Japan ..................... | 568/802 |
| 6605605 | 10/1967 | Netherlands ............ | 568/802 |
| 1222992 | 2/1971 | United Kingdom . | |

OTHER PUBLICATIONS

Chem.–Ing.–Tch., vol. 62, 1990, No. 12, pp. 1041–1043; "Reaktionskinetik und Reaktionstechnik der Brenzcatechin–. . . ", Z. Kricsfalussy et al.

Erdol und Kohle, Erdgas, Petrochemie; 1978/1979, pp. 507–524; "Wege zum Propylenoxid", H. Waldmann et al, Oct. 6, 1978.

Zhurnal Obshchei Khimii, vol. 30, No. 5, pp. 1629–1633; "Catalytic Oxidation of Aliphatic Amines with . . . " L. L. Lebedev et al, Feb. 3, 1959.

Primary Examiner—Werren B. Lone
Attorney, Agent, or Firm—William C. Gerstenzang; Sprung Horn Kramer & Woods

[57] ABSTRACT

Organic compounds are selectively oxidized by means of a particularly advantageous process, using elemental oxygen and a catalyst containing palladium and copper and carrying out the process in the presence of carbon monoxide.

9 Claims, No Drawings

CATALYTIC OXIDATION

The present invention relates to an improved process for the selective catalytic oxidation of organic compounds.

It is known that organic compounds can be selectively oxidized with active oxygen compounds. Suitable active oxygen compounds are, for example, hydrogen peroxide, percarboxylic acids or alkyl hydroperoxides. Thus, for example, propylene oxide can be selectively obtained from propylene and alkyl hydroperoxides in the presence of organomolybdenum compounds (see Erdöl Kohle, Erdgas, Petrochemie 1978/79, p. 507), dihydroxybenzenes can be selectively obtained from phenol and hydrogen peroxide or percarboxylic acids [see Chem. Ing. Techn. 62 (12), 1 041 (1990)] and cyclohexanone oxime can be selectively obtained from cyclohexanone, ammonia and hydrogen peroxide (O. L. Lebedev und S. N. Kazarnovskii, Zh. Obshck Khim., 30, (1960), 1631).

A disadvantage of these processes is the use of oxidizing agents which are relatively difficult to prepare and therefore expensive. In the case of alkyl hydroperoxides, there is the additional fact that the alcohol corresponding to the alkyl hydroperoxide used is formed as a coupled product. This then has to be fed to an independent use or be recycled after reconversion into It has now been found that organic compounds can be selectively oxidized by elemental oxygen, if the process is carried out in the presence of a catalyst containing palladium and copper and in the presence of carbon monoxide.

Organic compounds which can be used are, for example, olefins. Suitable olefins are, for example, those of the formula (I)

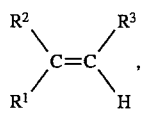

in which $R^1$, $R^2$ and $R^3$ are identical or different and are each hydrogen, straight-chain or branched $C_1$-$C_{12}$-alkyl, $C_5$-$C_6$-cycloalkyl or phenyl, where alkyl, cycloalkyl and phenyl radicals can optionally be substituted by up to 3 identical or different substituents selected from the group consisting of hydroxyl, formyl, carboxyl, fluoro, chloro, bromo, nitro and acetamino radicals and where $R^1$ and $R^3$ can also together be a hydrocarbon bridge having up to 10 carbon atoms.

Preferred olefins are unsubstituted, straight-chain and cyclic olefins having 2–8 carbon atoms. Particularly preferred olefins are ethylene, propylene, 1-butene, 2-butene, 1-n-octene and cyclopentene.

Use of olefins gives the corresponding epoxides. If the process is carried out in the presence of water, the corresponding glycols are obtained, in the presence of carboxylic acids, the corresponding glycol esters are obtained.

Organic compounds which can be used also include aromatics. Suitable aromatics are, for example, those of the formula (II)

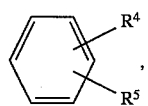

in which $R^4$ and $R^5$ are identical or different and are each hydrogen, straight-chain or branched $C_1$-$C_{12}$-alkyl, hydroxyl, fluorine, chlorine or bromine.

Preferred aromatics are toluene, xylene, ethylene, n-propylbenzene, i-butylbenzene, phenol and chlorobenzene. Particularly preferred aromatics are toluene, phenol and chlorobenzene, in particular phenol.

Use of aromatics gives the corresponding ring-hydroxylated derivatives, with the OH groups preferably being introduced in the o- or p-position.

Particularly preferably, a mixture of catechol and hydroquinone are prepared from phenol.

Organic compounds which can be used also include cyclic ketones. Suitable cyclic ketones are, for example, those of the formula (III)

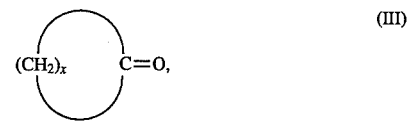

in which x is an integer from 3 to 11.

Preference is given to cyclohexanone.

Use of cyclic ketones Gives the corresponding lactones, for example, cyclohexanone gives ε-caprolactone.

Cyclic ketones, for example those of the formula (III), can also be reacted in the presence of ammonia in the manner of the invention. Thus, for example, cyclohexanone and ammonia give cyclohexanone oxide which optionally reacts further, completely or partially, to give ε-caprolactam.

Organic compounds which can be used also include linear ketones. Suitable linear ketones are, for example, those of the formula (IV)

in which $R^6$ and $R^7$ are identical or different and are each methyl, ethyl, n-propyl or cyclohexyl.

Preference is given to acetone.

Use of linear ketones gives, if the process is carried out in the presence of aremona, the corresponding azines, for example acetone gives acetazine.

It is an essential feature of the process of the invention that it is carried out in the presence of a catalyst containing palladium and copper. The palladium can, for example, be present in the form of the chloride, bromide, acetate or as metal, the copper can, for example, be present as copper (I) chloride, copper (II) chloride, copper(I) bromide, copper(I) oxide, copper(II) oxide or as metal. Copper can also be used in the form of a eutectic salt melt, for example a salt melt comprising copper (II) chloride and potassium chloride.

In carrying out the process of the invention, the catalyst constituents can be added as they are obtained to the reaction mixture. It is also possible to apply one or both constituents to a support material, for example to aluminium oxide, silicon dioxide, titanium dioxide, niobium pentoxide, tantalum oxide, carbon, etc.

Such supported catalysts can contain, for example, from 1 to 100 g/l of catalytically active substance. Supported catalysts can, for example, be used arranged in a fixed bed or in suspended form.

The ratio of palladium to copper can be varied within wide limits. Calculated as metal, the equivalent ratio of palladium to copper can be, for example, from 1:1 to 1:1 000. This ratio is preferably in the range from 1:1 to 1:100, particularly preferably in the range from 1:1 to 1:10.

The process of the invention is generally carried out at elevated temperature, for example at 50°–150° C. Preference is given to temperatures in the range from 60° to 120° C., in particular in the range from 80° to 100° C.

The process of the invention can be carried out at a variety of pressures, for example in the range from 1 to 100 bar. Pressures are preferably in the range from 5 to 80 bar, in particular in the range from 20 to 60 bar. A higher pressure generally gives a higher reaction rate.

The elemental oxygen can be used as technical grade oxygen gas, in the form of air or in admixture with inert gases, for example in admixture with nitrogen and/or carbon dioxide. Oxygen-containing gas mixtures can contain, for example, from 2 to 60% by volume of oxygen.

Carbon monoxide can be used in the available grades.

In general, one mole or less of oxygen and one mole or less of carbon monoxide are used per mole of organic compound to be oxidized. Preference is given to using an excess of the organic compound (based on oxygen) and an excess of carbon monoxide (based on oxygen), but no larger molar amount of carbon monoxide than of organic compound to be oxidized. For example, the organic compound, carbon monoxide and oxygen can be used in molar ratios of 1: (1 to 0.01):(1 to 0.01). The molar ratios are preferably 1:(0.5 to 0.02):(0.5 to 0.02). Even with these relative amounts used, the explosive limits of the respective system must, of course, be taken into account; these can, if desired, be altered by addition of inert gases, for example nitrogen and/or carbon dioxide.

In an example of carrying out the process, for each mole of phenol, from 0.01 to 0.5 mol of $Cu_2Cl_2$ and from 0.0001 to 0,1 mol of $PdCl_2$ are reacted at from 80° C. to 120° C. with a gas mixture of CO and air having a molar CO content of from 0.01 to 0.5 mol and a molar oxygen content of from 0.01 to 0.5 mol at a system pressure of from 30 to 80 bar, with a reaction mixture containing 7–10% by weight of catechol and hydroquinone being obtained in from 3 to 12 hours.

The work-up of the reaction mixtures is carried out in a manner known per se. For example, after filtration and extraction with organic solvents, the isolation of starting materials and products can be effected by distillation.

The process of the invention can be carried out in the various known types of reactor. It can, for example, be carried out continuously in a bubble column or continuously or batchwise in a stirred reactor. Suitable materials for the reactors are, for example, corrosion-resistant stainless steels, enamelled steels, glass or special metals such as tantalum.

The process of the invention has the main advantage that it allows a wide variety of organic compounds to be selectively oxidized with the oxidizing agent which is the simplest and cheapest to obtain.

EXAMPLES

Example 1

A steel container provided with a tantalum insert and fitted with a gassing stirrer, baffle, thermocouple and pressure maintenance device was charged with 94 g of phenol, 10 g of dry palladium chloride, 45 g of copper(I) chloride and 4 g of water. 12 l/h of carbon monoxide and 14 l/h of air were metered into the vessel at 100° C. The pressure was maintained at 50 bar. After a reaction time of 4 hours, the reaction mixture contained 1% by weight of catechol and 1% by weight of hydroquinone, after a reaction time of 9 hours it contained 4.1% by weight of catechol and 2.9% by weight of hydroquinone. The selectivity of the conversion of phenol into catechol and hydroquinone was over 95%. A small amount of chloro-phenols was obtained as a byproduct.

Example 2 (for comparison)

Example 1 was repeated, but not using any palladium chloride. After 9 hours, analysis found no catechol and no hydroquinone in the reaction mixture.

Example 3 (for comparison)

Example 1 was repeated, but not using any copper(I) chloride. After 9 hours, the reaction mixture contained no catechol and only 0.5% by weight of hydroquinone.

Example 4 (for comparison)

Example 1 was repeated, but no carbon monoxide was metered in. After 9 hours, analysis found only traces of catechol and hydroquinone in the reaction mixture.

Example 5

Example 1 was repeated, but without addition of water. After 9 hours, analysis found 0.8% by weight of catechol and 0.2% by weight of hydroquinone in the reaction mixture.

Example 6

The apparatus described in Example 1 was charged with 78 g of benzene, 10 g of dry palladium chloride, 45 g of copper(I) chloride and 9 g of water. 12 l/h of carbon monoxide and 14 l/h of air were metered into the vessel at 100° C. The pressure was maintained at 25 bar. After a reaction time of 13 hours, the reaction mixture contained 3% by weight of phenol. No other byproducts were formed.

Example 7

The apparatus described in Example 1 was charged with 92 g of toluene, 10 g of dry palladium chloride, 45 g of copper(I) chloride and 9 g of water. 12 l/h of carbon monoxide and 14 l/h of air were metered into the vessel at 180° C. The pressure was maintained at 50 bar. After a reaction time of 4 burs, the reaction mixture contained 0.34% by weight of o-cresol, 0.10% by weight of m-cresol, 0.18% by weight of p-cresol and 0.18% by weight of benzaldehyde. The selectivity of the conversion of toluene to the cresols and benzaldehyde was 90%.

What is claimed is:

1. A process for the selective oxidation of an aromatic compound to the corresponding ring-hydroxylated derivative, which consists essentially of carrying out said selective oxidation using elemental oxygen in the presence of carbon monoxide and a catalyst containing palladium and copper at a temperature of 50° to 150° C. and a pressure of 1–100 bar.

2. The process of claim 1, in which the organic compound is selected from the group consisting of olefins, aromatics, cyclic ketones and linear ketones.

3. The process of claim 1, in which the organic compound is selected from aromatics represented by the formula

(II)

in which $R^4$ and $R^5$ are identical or different and are each hydrogen, straight-chain or branched $C_1$-$C_{12}$-alkyl, hydroxyl, fluorine, chlorine or bromine.

4. The process of claim 3, in which the equivalent ratio of palladium to copper is 1:1 to 1:1000.

5. The process of claim 3, in which the molar ratio of organic compound to carbon monoxide to oxygen is 1:(1 to 0.01):(1 to 0.01).

6. The process of claim 3, in which the organic compound is phenol.

7. The process of claim 3, in which the organic compound is benzene.

8. The process of claim 3, in which the organic compound is toluene.

9. The process of claim 1 wherein said selective oxidation is carried out in a reactor fitted with a gassing stirrer, and said oxygen and carbon monoxide is introduced through said stirrer.

* * * * *